US008560059B2

(12) United States Patent
Hoarau et al.

(10) Patent No.: US 8,560,059 B2
(45) Date of Patent: Oct. 15, 2013

(54) SYSTEM AND METHODS FOR OPTICAL SENSING AND DRUG DELIVERY USING MICRONEEDLES

(75) Inventors: Carine Hoarau, Lafayette, CA (US); Li Li, Milpitas, CA (US); Keith Batchelder, San Francisco, CA (US); Shannon E. Campbell, Oakland, CA (US)

(73) Assignee: Covidien LP, Mansfield, MA (US)

( * ) Notice: Subject to any disclaimer, the term of this patent is extended or adjusted under 35 U.S.C. 154(b) by 1195 days.

(21) Appl. No.: 11/716,145

(22) Filed: Mar. 9, 2007

(65) Prior Publication Data

US 2008/0221408 A1    Sep. 11, 2008

(51) Int. Cl.
*A61N 1/30* (2006.01)
*A61M 5/32* (2006.01)
*A61B 17/20* (2006.01)

(52) U.S. Cl.
USPC .................. 604/20; 604/272; 604/21; 604/22

(58) Field of Classification Search
USPC ................................ 604/20–22, 272, 239, 48
See application file for complete search history.

(56) References Cited

U.S. PATENT DOCUMENTS

| | | | |
|---|---|---|---|
| 4,306,612 A | 12/1981 | Baker et al. | |
| 4,651,934 A | 3/1987 | Bender et al. | |
| 4,681,395 A | 7/1987 | Lindsay et al. | |
| 4,703,175 A | 10/1987 | Salour et al. | |
| 4,709,413 A | 11/1987 | Forrest et al. | |
| 4,711,525 A | 12/1987 | Feth | |
| 4,793,708 A | 12/1988 | Bednarz | |
| 4,911,167 A | 3/1990 | Corenman et al. | |
| 4,924,870 A | 5/1990 | Wlodarczyk et al. | |
| 5,020,912 A | 6/1991 | Pavlath | |
| 5,079,845 A | 1/1992 | Childers | |
| 5,089,697 A | 2/1992 | Prohaska | |

(Continued)

FOREIGN PATENT DOCUMENTS

| | | |
|---|---|---|
| DE | 19606025 | 8/1997 |
| WO | WO 99/07277 | 2/1999 |
| WO | WO 2004/044557 A2 | 5/2004 |

OTHER PUBLICATIONS

De Backer, Daniel, et al., "Microvascular Blood Flow Is Altered in Patients with Sepsis," American Journal of Respiratory and Critical Care Medicine, vol. 166, pp. 98-104, (2002), http://ajrccm.atsjournals.org/cgi/content/full/166/1/98, Last accessed Feb. 16, 2007.

(Continued)

*Primary Examiner* — Kevin C Sirmons
*Assistant Examiner* — Bradley G Thomas, Jr.
(74) *Attorney, Agent, or Firm* — Fletcher Yoder, P.C.

(57) ABSTRACT

The current techniques provide a system for monitoring a physiological parameter of a patient using microneedles that are coupled to an optical system, allowing spectroscopic measurements to be made immediately below the outer layer of the epidermis. In embodiments of the present invention, the results of the spectroscopic measurements are used to control the administration of a drug through an intravenous tube. In other embodiments, the microneedles may be coated with a drug for administration to the patient. In other embodiments, the microneedles may be mounted in a probe, wherein an actuator is used to move the needles into contact with the skin, and a drug delivery system is used to infuse the drug into the patient. A method for making needles is also provided.

9 Claims, 9 Drawing Sheets

(56) References Cited

U.S. PATENT DOCUMENTS

| | | | |
|---|---|---|---|
| 5,118,931 A | 6/1992 | Udd et al. | |
| 5,148,303 A | 9/1992 | Biard | |
| 5,196,714 A | 3/1993 | Garcia, Jr. et al. | |
| 5,214,487 A | 5/1993 | Pavlath et al. | |
| 5,286,980 A | 2/1994 | Richert | |
| 5,300,769 A | 4/1994 | Dahlin et al. | |
| 5,354,825 A | 10/1994 | Klainer et al. | |
| 5,355,208 A | 10/1994 | Crawford et al. | |
| 5,374,821 A | 12/1994 | Muhs et al. | |
| 5,401,954 A | 3/1995 | Richert | |
| 5,480,723 A | 1/1996 | Klainer et al. | |
| 5,486,921 A | 1/1996 | Priest | |
| 5,598,489 A | 1/1997 | Pavlath et al. | |
| 5,645,059 A | 7/1997 | Fein et al. | |
| 5,698,848 A | 12/1997 | Belk | |
| 5,700,897 A | 12/1997 | Klainer et al. | |
| 5,777,737 A | 7/1998 | Priest | |
| 5,780,847 A | 7/1998 | Dawson et al. | |
| 5,853,364 A | 12/1998 | Baker, Jr. et al. | |
| 5,854,678 A | 12/1998 | Liu et al. | |
| 5,898,496 A | 4/1999 | Huang et al. | |
| 5,949,930 A | 9/1999 | Cordova et al. | |
| 5,973,783 A | 10/1999 | Goldner et al. | |
| 5,991,026 A | 11/1999 | Kluth et al. | |
| 6,152,059 A | 11/2000 | Del Raso | |
| 6,197,257 B1 | 3/2001 | Raskas | |
| 6,219,575 B1 | 4/2001 | Nemati | |
| 6,256,533 B1 | 7/2001 | Yuzhakov et al. | |
| 6,271,766 B1 | 8/2001 | Didden et al. | |
| 6,312,612 B1 | 11/2001 | Sherman et al. | |
| 6,334,856 B1* | 1/2002 | Allen et al. | 604/191 |
| 6,379,324 B1 | 4/2002 | Gartstein et al. | |
| 6,418,260 B1 | 7/2002 | Komachiya et al. | |
| 6,451,240 B1* | 9/2002 | Sherman et al. | 264/504 |
| 6,503,231 B1 | 1/2003 | Prausnitz et al. | |
| 6,535,753 B1 | 3/2003 | Raskas | |
| 6,549,796 B2 | 4/2003 | Sohrab | |
| 6,563,589 B1 | 5/2003 | Bennett et al. | |
| 6,591,124 B2 | 7/2003 | Sherman et al. | |
| 6,652,478 B1 | 11/2003 | Gartstein et al. | |
| 6,663,820 B2 | 12/2003 | Arias et al. | |
| 6,671,527 B2 | 12/2003 | Petersson et al. | |
| 6,738,654 B2 | 5/2004 | Sohrab | |
| 6,743,211 B1 | 6/2004 | Prausnitz et al. | |
| 6,774,354 B2 | 8/2004 | Ames | |
| 6,790,179 B2 | 9/2004 | Skover | |
| 6,804,008 B1 | 10/2004 | Morison et al. | |
| 6,811,307 B2 | 11/2004 | Crowe et al. | |
| 6,815,360 B1* | 11/2004 | Canham et al. | 438/706 |
| 6,840,910 B2 | 1/2005 | Skover | |
| 6,855,117 B2 | 2/2005 | Skover | |
| 6,904,301 B2 | 6/2005 | Raskas | |
| 6,931,277 B1 | 8/2005 | Yuzhakov et al. | |
| 7,004,928 B2 | 2/2006 | Aceti et al. | |
| 7,009,707 B2 | 3/2006 | Beresford et al. | |
| 7,042,572 B2 | 5/2006 | Lange et al. | |
| 7,046,888 B2 | 5/2006 | Ye et al. | |
| 2002/0058863 A1 | 5/2002 | Petersson et al. | |
| 2002/0133129 A1 | 9/2002 | Arias et al. | |
| 2002/0169411 A1 | 11/2002 | Sherman et al. | |
| 2002/0177764 A1 | 11/2002 | Sohrab | |
| 2003/0083558 A1 | 5/2003 | Skover | |
| 2003/0120179 A1 | 6/2003 | Skover | |
| 2003/0130569 A1 | 7/2003 | Raskas | |
| 2003/0153900 A1 | 8/2003 | Aceti et al. | |
| 2003/0158472 A1 | 8/2003 | Sohrab | |
| 2004/0039269 A1 | 2/2004 | Ward et al. | |
| 2004/0039343 A1* | 2/2004 | Eppstein et al. | 604/200 |
| 2004/0106163 A1 | 6/2004 | Workman, Jr. et al. | |
| 2004/0146611 A1 | 7/2004 | Arias et al. | |
| 2004/0162473 A1 | 8/2004 | Sohrab | |
| 2004/0260162 A1 | 12/2004 | Rohleder et al. | |
| 2005/0209565 A1 | 9/2005 | Yuzhakov et al. | |
| 2005/0277887 A1* | 12/2005 | Douglas et al. | 604/173 |
| 2005/0283057 A1 | 12/2005 | Raskas | |
| 2006/0074282 A1 | 4/2006 | Ward et al. | |
| 2006/0094985 A1 | 5/2006 | Aceti et al. | |
| 2006/0116563 A1 | 6/2006 | Asano et al. | |
| 2007/0276211 A1* | 11/2007 | Mir et al. | 600/345 |

OTHER PUBLICATIONS

George Tech Research News, "Microneedles: Report Describes Progress in Developing New Technology for Painless Drug and Vaccine Delivery," Nov. 17, 2003, http://gtresearchnews.gatech.edu/newsrelease/needlespnas.htm, Last accessed Jan. 19, 2007.

George Tech Research News, "Taking the 'Ouch' Out of Needles: Arrays of Micron-Scale "Microneedles" Offer New Technique for Drug Delivery", Jun. 22, 1998, http://gtresearchnews.gatech.edu/newsrelease/NEEDLES.html, Last accessed Jan. 19, 2007.

Lee, Sanghoon, et al., "Microfluidic valve with cored glass microneedle for microinjection," The Royal Society of Chemistry 2003, Lab Chip, 2003, vol. 3, pp. 164-167.

Martanto, Wijaya, et al. "Fluid Dynamics in Conically Tapered Microneedles," AIChE Journal, pp. 104-113, Jun. 2005, pp. 1599-1607, vol. 51, No. 6. www.interscience.wiley.com.

Martanto, Wijaya, et al. "Microinfusion Using Hollow Microneedles," *Pharmaceutical Research*, vol. 23, No. 1, Jan. 2006, Springer Science + Business Media, Inc.

Prausnitz, Mark R., Microneedle Technology for Medical Applications, Abstract, 2 pages, Jun. 5, 2006, presented in Pleasanton, California.

Prentice, Paul, et al., Membrane disruption by optically controlled microbubble cavitation, vol. 1, Nov. 2005, Nature Physics, www.nature.com/naturephysics.

Wang, Ping, PhD, et al. "Minimally Invasive Extraction of Dermal Interstitial Fluid for Glucose Monitoring Using Microneedles," Diabetes Technology & Therapeutics, pp. 131-141, vol. 7, No. 1, 2005. School of Chemical and Biomolecular Engineering and Institute for Bioengineering and Bioscience, Georgia Institute of Technology, Atlanta, Georgia.

* cited by examiner

SYSTEM AND METHODS FOR OPTICAL SENSING AND DRUG DELIVERY USING MICRONEEDLES

BACKGROUND OF THE INVENTION

1. Field of the Invention

The present technique relates generally to monitoring a physiological parameter of a patient. Specifically, the present technique is directed to the use of microneedles in physiological monitoring and drug delivery.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, caregivers, such as doctors and nurses, desire to discover ailments in a timely manner in order to better care for patients. The passage of time prior to discovering an ailment may limit treatment options and, in some instances, may lead to irreversible damage. If an ailment is discovered early enough, however, a variety of remedial options and corrective actions may be initiated in order to treat the condition and prevent further damage to the health of the patient. Accordingly, healthcare professionals are continuously pursuing methods to expedite the diagnosis of a problem or to anticipate a potential problem in order to better serve their patients.

For example, a severe localized infection in a patient may lead to sepsis, or a generalized infection of the blood. Examples of such infections include urinary tract infections, infections of the liver or gall bladder, peritonitis, cellulitis, and bacterial pneumonia, among others. As the prognosis may be poor, an early determination that sepsis has set in is crucial for a positive outcome.

An early symptom of the development of sepsis is a decrease in microvascularization, or blood flow through the capillaries. While large vessels may be continuously perfused, smaller vessels decrease in density during sepsis. Currently, techniques to monitor bulk perfusion of a patient exist, such as pulse oximetry, but there is no objective, reliable, and accurate method for assessing the disruption of microvascularization.

Once sepsis has been diagnosed, early treatment may determine whether a favorable outcome is reached. As this treatment may involve large doses of broad spectrum antibiotics and compounds intended to increase blood flow to the capillaries, it is important to determine that sepsis is present before starting treatment to avoid unnecessary drug administration. The technique used to deliver the medicine may also be affected by the patient's condition.

Currently, three primary methods are used to deliver pharmacologically active substances into a patient: oral ingestion, injection, and transdermal absorption. While other methods exist, such as nasal sprays, inhalation systems, and through skin air-driven injections, most may be thought of as variations of the methods above. All three methods have limitations that make their use dependent on the patient's condition and the drug selected. For example, the decrease in microvascular circulation caused by some conditions, such as sepsis, may limit transdermal absorption. Further, persons in sepsis may not be able to consume drugs for treatment.

Furthermore, for conditions such as sepsis it may be desirable to measure a physiological characteristic of a patient (such as the microvascular response) or a chemical concentration of a compound in a patient in conjunction with drug delivery. Drug delivery approaches, such those described above, are typically not easily integrated with current monitoring techniques.

Accordingly, there would be significant value in a system that could be used to monitor localized physiological parameters. Such a technique would be especially useful in conjunction with the administration of pharmacologic substances.

SUMMARY

Certain aspects commensurate in scope with the originally claimed invention are set forth below. It should be understood that these aspects are presented merely to provide the reader with a brief summary of certain forms of the invention might take and that these aspects are not intended to limit the scope of the invention. Indeed, the invention may encompass a variety of aspects that may not be set forth below.

One embodiment of the present techniques provides an array of microneedles, at least one of which is optically transmissive. In one aspect, the optically transmissive microneedles are coupled to a photoemitter and detector for spectroscopic measurements.

Another embodiment provides a system for patient care comprising a microneedle array of one or more microneedles, wherein at least one of the microneedles is optically transmissive. At least one of the optically transmissive microneedles is in optical communication with an optical detection device. The system has control unit comprising a data analysis unit configured to receive a measurement signal generated by the optical detection device.

Another embodiment provides a method for monitoring patient status comprising placing a microneedle array made up of one or more microneedles on the epidermis of a patient. At least one of the microneedles is in optical communication with an optical emission component, an optical detection component, or both. The signal obtained from the optical detection component is analyzed to determine a physiological parameter of the patient.

Another embodiment provides a method for manufacturing a microneedle array, comprising forming one or more microneedles from a substrate material, and coupling at least one of the microneedles to at least one of a photoemitter or a detector.

BRIEF DESCRIPTION OF THE DRAWINGS

Advantages of the invention may become apparent upon reading the following detailed description and upon reference to the drawings in which.

DETAILED DESCRIPTION OF SPECIFIC EMBODIMENTS

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

I. Overview

The present techniques allow the monitoring of the concentration of substances in a localized area immediately below the epidermis of a patient. Such monitoring may be beneficial in the diagnosis and treatment of sepsis and/or other conditions requiring localized or continuous determination of the concentration of substances in a patient. In the techniques, optical microneedles (i.e., microneedles having optically transmissive elements or formed from optically transmissive materials) are optically coupled to a spectroscopic system. The optical microneedles are used to pierce the outermost layer of cells of the skin, or stratum cornea, allowing the spectroscopic system to analyze the concentration of substances immediately under the stratum cornea.

The monitoring of the concentration of substances under the stratum cornea may allow the administration of drugs to be closely controlled. For example, the spectroscopic system may be linked to pumps controlling the administration of compounds through intravenous drip tubes. This may allow treatment of conditions to be more closely controlled, which may improve the prognosis.

Drug-delivery microneedles may be directly used for the delivery of pharmacologically active compounds. For example, the microneedles may be coated with such compounds such that, upon insertion, the compound is introduced into the interstitial space beneath the stratum cornea. In another technique, as the microneedles may increase the permeability of the epidermis by a factor of 25,000 or more, drugs on the surface of the skin may be directly diffused into a patient. Finally, hollow microneedles may be used for the direct injection of drugs.

The techniques discussed below also disclose general methods for manufacturing microneedles that may be used to implement the monitoring and drug delivery methods discussed above. These methods include techniques for making both hollow and solid microneedles.

II. A Microneedle Array Coupled to a Spectrosopic System

Figure 1:
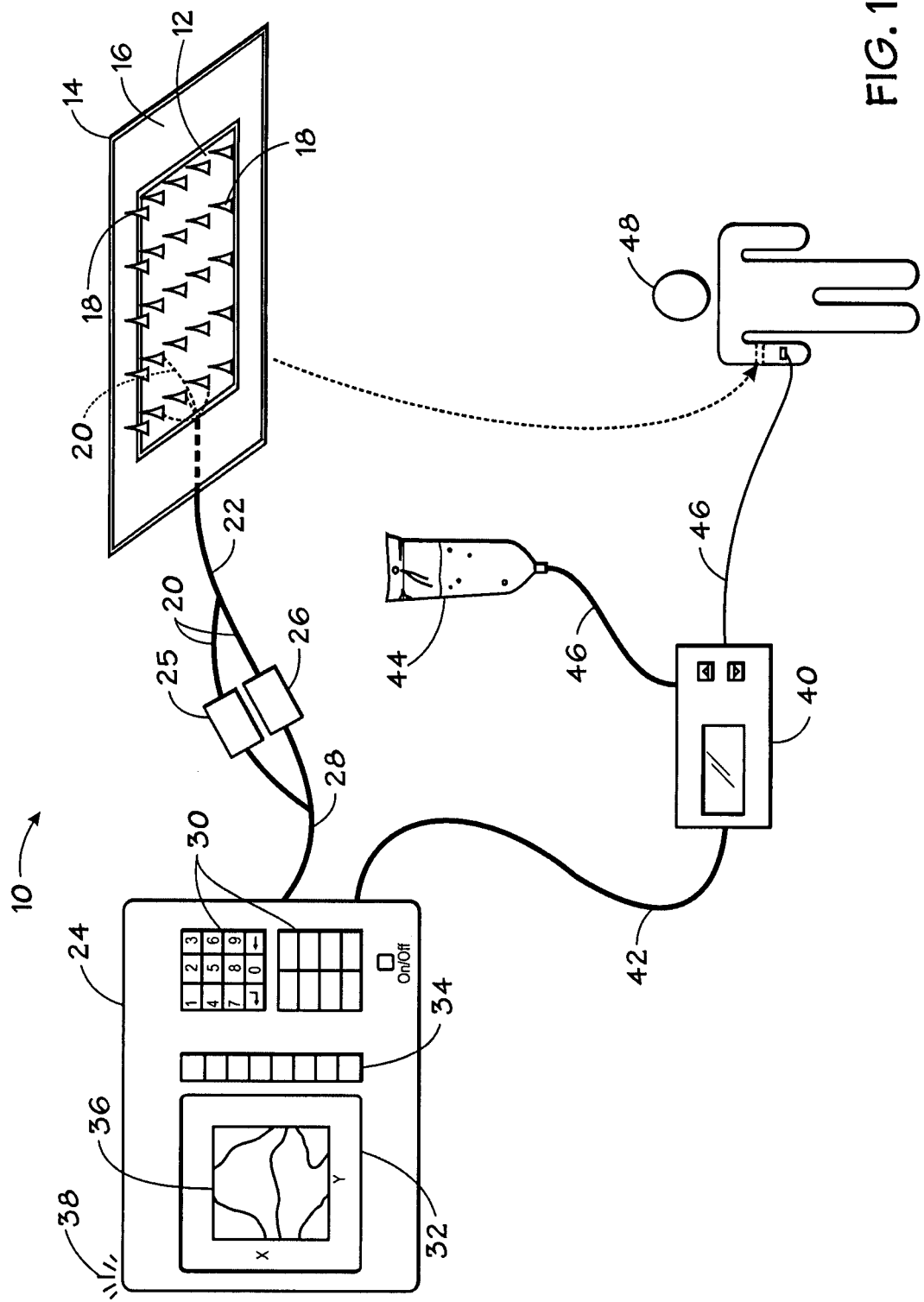
FIG. 1 is a perspective drawing of a microneedle array in which several of the microneedles are coupled to optical fibers for connection to a spectroscopic data analysis and control unit in accordance with embodiments of the present technique.

A prospective view of a microneedle array system 10 that may be used for monitoring the concentration of substances below the stratum cornea of a patient is shown in FIG. 1. In this system a microneedle array 12 is attached to a backing material 14 which has an adhesive 16 designed to hold the microneedle array system 10 in place against the surface of the skin. The microneedle array 12 comprises a series of microneedles 18 which are formed from a coating material.

In the depicted embodiment, the microneedles 18 are coupled to one or more optical fibers 20 for use in spectroscopic analysis of the tissue into which the microneedles 18 project. In an embodiment of the present techniques, the optical fibers 20 may be connected to emitters 25 and detectors 26 attached to the microneedle array 12. The emitters 25 and detectors 26 are connected to the spectroscopic analysis unit 24 by electrical lines 28. In another embodiment, the emitters 25 and detectors 26 may be contained in the spectroscopic analysis unit 24 and connected directly to the microneedles by the optical fibers 20 contained within the optical fiber cable 22. In another embodiment, the microneedles 18 may be directly coupled to one or more arrays of emitters 25 and detectors 26 mounted on the back of the microneedle 12 and connected to the spectroscopic analysis unit 24 through electrical lines 28. Those skilled in the art will realize that the emitters 25 and detectors 26 do not have to be mounted in the same unit. For example, in embodiments the emitters 25 may be mounted within the spectroscopic analysis unit 24, while the detectors 26 are mounted on the microneedle array 12.

The backing material 14 may be any such material typically used in a medical context, such as a medical grade polymer, a nylon mesh, or a polyurethane polymer. Those skilled in the art will recognize that any number of other backing materials 14 may be used, such as cloth or other materials, while remaining within the scope of the current disclosure. In embodiments of the present techniques, the adhesive 16 may be a medical grade adhesive, such as a silicone polymer, among others.

In certain embodiments the microneedle array system 10 may contain one or more microneedles 18 that are coated with drugs for administration via application of the microneedle array 12 to a patient. Such drugs may include compounds to increase microvascular blood flow, such as acetylcholine. Other compounds may also be used, including such compounds as anti-inflammatory compounds, substances used to affect blood sugar levels, or antibiotics, among others. Those skilled in the art will recognize that any number of potential drugs may be used in embodiments of the current technique.

All or part of the microneedles 18 that are coupled to an optical system may be made from or may incorporate a light transmissive material, e.g., an optically transparent or semi-transparent material, such as a polycarbonate, an acrylic polymer, a glass, a silicone, or other light transmissive materials. Those skilled in the art will recognize that any number of light transmissive materials may be used to form the microneedles in embodiments of the present techniques, while remaining within the scope of this disclosure.

A spectroscopic analysis utilizing light transmissive microneedles may include techniques to measure oxygen saturation, tissue hydration, sugar concentration, lipid concentration, the concentration of a drug, or any other physiological parameter of interest. For example, in one embodiment of the present techniques, a microneedle array 12 coupled to arrays of emitters 25 and detectors 26 may be used to generate a map of the microvascular blood flow. This may be performed by using a standard pulse oximetry algorithm to calculate the oxygen saturation, or $SpO_2$, at each microneedle 18. In one common technique, a signal from a detector is conditioned and processed to determine the ratio of modulation ratios (ratio of ratios) of red to infrared signals. This modulation ratio has been observed to correlate with arterial oxygen saturation. The pulse oximeters and sensors may be empirically calibrated by measuring the modulation ratio over a range of in vivo measured arterial oxygen saturations ($SaO_2$) on a set of patients, healthy volunteers, or animals. The observed correlation is used in an inverse manner to estimate blood oxygen saturation ($SpO_2$) based on the measured value of modulation ratios of a patient. For example, techniques for estimation of oxygen saturation using modulation ratios are described in U.S. Pat. Nos. 5,853,364, and 4,911,167, both of which are incorporated herein by reference in their entirety. Furthermore, the relationship between oxygen saturation and modulation ratio is further described in U.S. Pat. No. 5,645,059, incorporated herein by reference in its entirety.

The spectroscopic analysis unit 24 may be specially designed for use with the microneedle array system 10 or may be a commercial unit adapted for use with such a microneedle array system 10. For example, in an embodiment of the present techniques, the spectroscopic analysis unit 24 may be a commercially available pulse oximeter, such as, for example, an OxiMax N-600® available from the Nellcor Puritan Bennett division of Tyco, which is configured for use in the microneedle array system 10. In one embodiment, such an oximeter is configured with a data port that may be used to send signals to other devices, such as an intravenous drug delivery pump 40. Such an oximeter may also be configured to connect to multiple emitters 25 and detectors 26, such as in a multiplexed system, as discussed below.

The spectroscopic analysis unit 24 may have controls 30 and a display 32 for the entry and display of analysis and control parameters. Such parameters may include the specific composition analysis desired, the wavelengths for the analysis, treatment control parameters, or other analysis parameters. Programmable keys 34 with legends displayed on the screen (so called "softkeys") may be provided in some embodiments.

Results 36 of the spectroscopic analysis, such as the map of microvascular circulation described above, may be shown on the display 32. In addition, an audible signal 38 may alert a practitioner to the presence of a condition or the initiation of treatment. The audible signal 38 may be in the form of one or more alarm tones or may be an annunciation of the results by a voice synthesizer. In addition to displaying the results 36, the spectroscopic analysis unit 24 may activate and/or control an intravenous pump 40 by a control line 42 attached to a data port (not shown). The intravenous pump 40 may be used to deliver one or more drugs from a storage container or drug reservoir, such as an I.V. drip bag 44, through tubing lines 46, to a patient 48. In one embodiment, the drugs are delivered to the patient through a standard intravenous drip. In another embodiment, as discussed below, the drugs may be delivered to the patient through the microneedle array 12.

III. Treatment Systems Using a Microneedle Array

Figure 2:
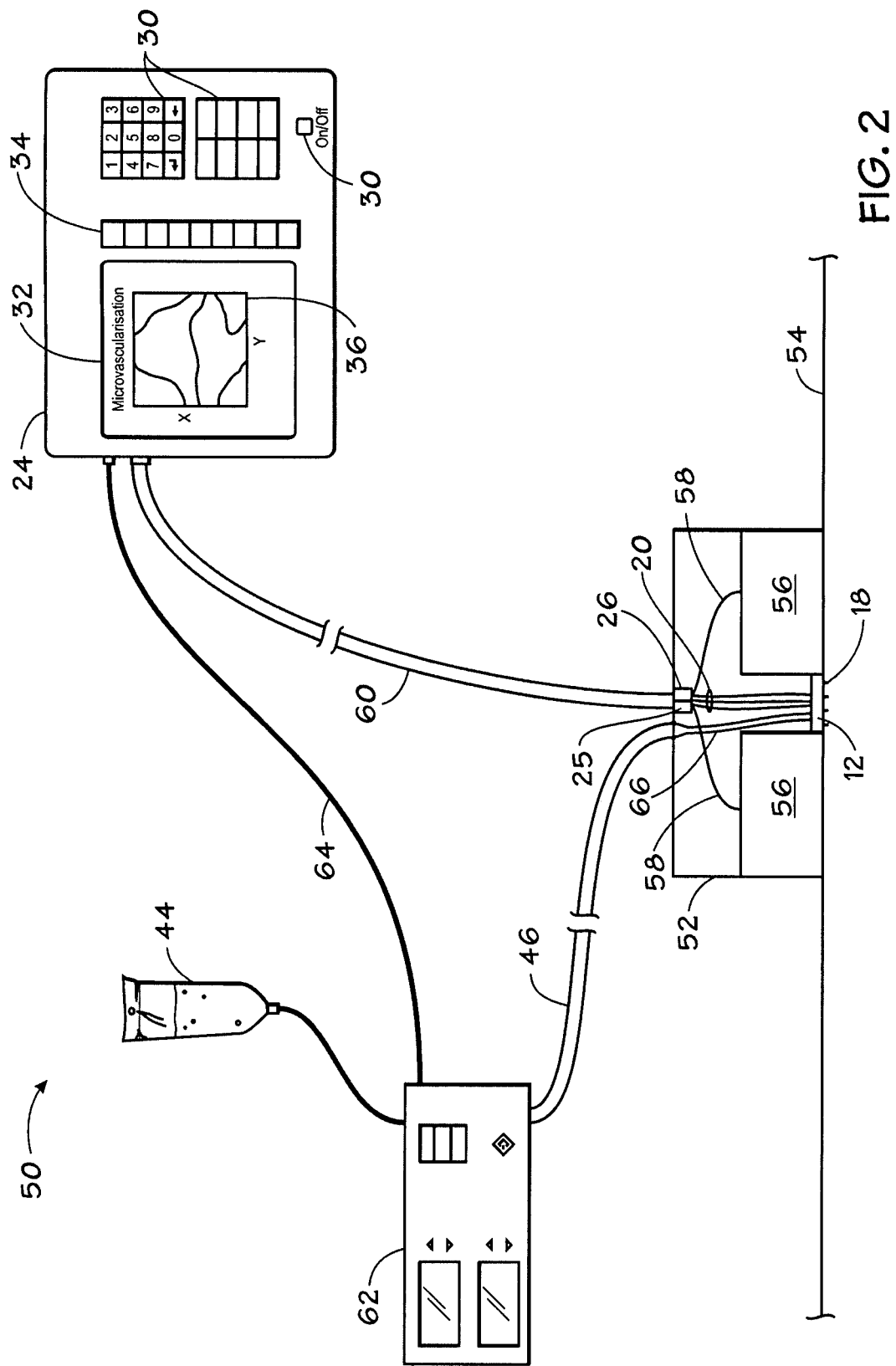
FIG. 2 is a perspective drawing of a system for measuring a physiological parameter of a patient and delivering a drug in which a microneedle array, shown by a cut away view, is coupled to both optical fibers and a drug delivery system in accordance with embodiments of the present technique.

A microneedle system 50 for monitoring a physiological parameter in or directly beneath the epidermis of a patient, while providing for simultaneous drug delivery is shown in by the perspective drawing FIG. 2. In this embodiment, the drug delivery is through the microneedles 18. In this system 50 the microneedle array 12 is carried in a probe 52, which is shown in a cut-away view. The probe 52 is placed on the patient 48. Actuators 56 contained within the probe 52 are used to advance the microneedle array 12, placing the microneedles 18 into contact with and piercing the epidermis 54 of the patient 48. In embodiments of the present invention the actuators 56 may move the microneedle array 12 appropriate distances for allowing drug infusion around the microneedles 18, as discussed with respect to FIG. 6 below. For example, such distances may be as low as 10 micrometers or less. The probe 52 contains electrical lines 58 to control the motion of the actuators 56.

In one embodiment, the probe 52 may contain emitters 25 and detectors 26, coupled to one or more microneedles 18 through fiber optics 20. The emitters 25, detectors 26, and actuators 56 are connected to a spectroscopic analysis unit 24 by a cable 60. In another embodiment, the spectroscopic analysis unit 24 may contain the optical systems. In this embodiment, fiber optics 20 in the cable 60 are used to couple the emitters 25 and detectors 26 in the spectroscopic analysis unit 24 to the microneedles 18. In another embodiment, the microneedles 18 are directly coupled to an array of emitters and detectors 26 mounted on the back of the microneedle array 12.

The spectroscopic analysis unit 24 is linked to a drug delivery pump 62 through a control cable 64. Under the control of the spectroscopic analysis unit 24, the drug delivery pump 62 transfers a drug from a storage container, such as I.V. drip bag 44, through tubing lines 46 to the probe 52. Inside the probe 52 the drug is transferred to the microneedle array 12 through a drug delivery line 66. The drug is then infused through the epidermis 54. Infusion of the drug through the epidermis may take place by creating a pool of the drug underneath the microneedle array 12, and then partially retracting the microneedles 18 under the control of the actuators 56 after the microneedles 18 have penetrated at least partially through the epidermis, as discussed with respect to FIG. 6, below. Alternatively the drug infusion may be performed by the use of microneedles 18 having a hollow core or one or more other passages through the microneedle 18, as discussed with respect to FIG. 7, below. Further, the drug delivery may be performed using an intravenous needle 68 in addition to, or instead of, the microneedle array 12. Such an embodiment may be useful to improve local conditions for sensing by the microneedle array 12, while administering medicines that have a global effect on the patient.

The spectroscopic analysis unit 24 may be used to control the amount of drug delivered to the patient 48 through the microneedles 18 on the basis of a spectroscopic analysis of one or more physiological parameters. Such parameters may include oxygen saturation, tissue hydration, sugar concentration, lipid concentration, the concentration of a drug, or any other physiological parameter of interest.

A. Components of a Microneedle System

Figure 3:
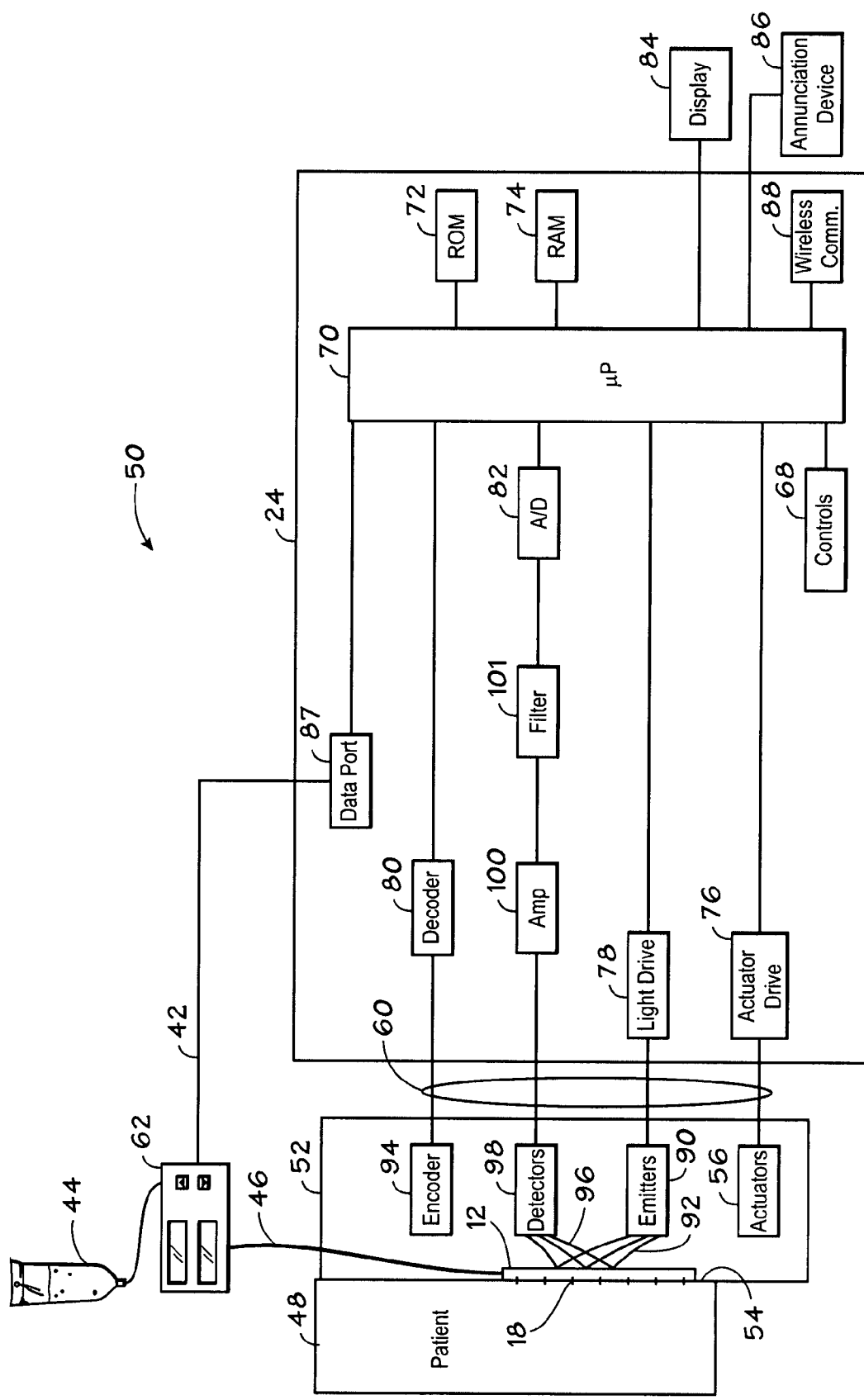
FIG. 3 is a block diagram of a spectroscopic system for using a microneedle array to monitor a physiological parameter and deliver a drug in accordance with embodiments of the present technique.
Figure 4:
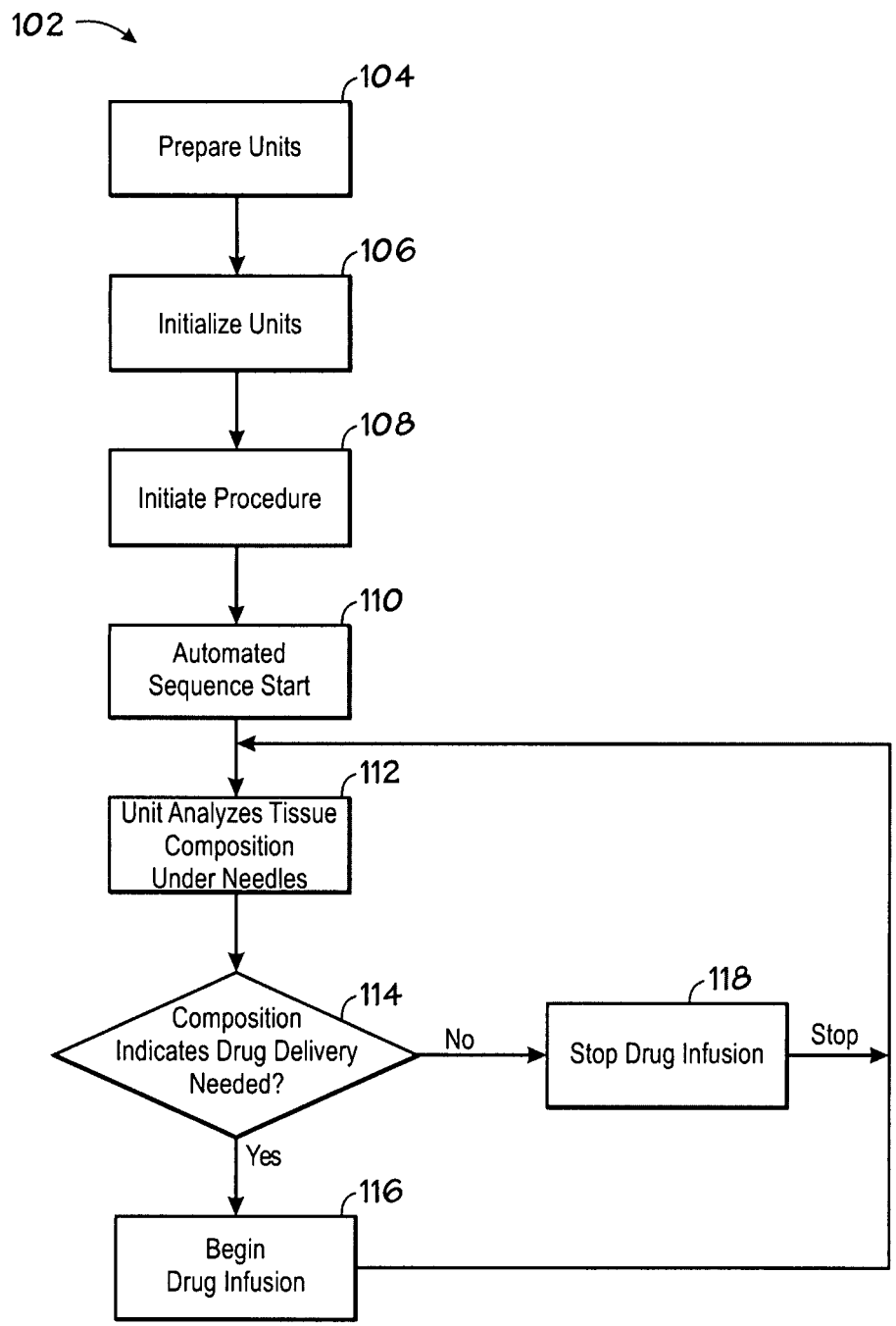
FIG. 4 is a flowchart of a procedure to monitor a physiological parameter of a patient and deliver a drug in response using a microneedle array.

A block diagram illustrating the components of the microneedle system 50 is shown in FIG. 3. As in FIG. 2, this embodiment shows the use of the microneedle array for the delivery of drugs. Those skilled in the art will recognize that the microneedle system 50 may use either the microneedles 18 or one or more intravenous needles for such delivery of drugs.

The microneedle system 50 has controls 68 to enable a practitioner to work with or control the operation of the spectroscopic analysis unit 24. For example, if a particular spectroscopic analysis unit 24 is configured to detect oxygen saturation for the determination of sepsis, a practitioner may input or select parameters, such as tissue type, target oxygen saturation, or baseline absorbance levels for the tissue that is to be measured, among others. Specifically, baseline parameters associated with various types of conditions may be stored in the spectroscopic analysis unit 24 and selected by a practitioner as a reference level for determining the sensitivity for alarming and treatment. Additionally, patient data may be entered, such as weight, age and medical history data. This information may be used to validate the baseline measurements or to assist in the understanding of anomalous readings.

The controls 68 are connected to a microprocessor 70 which calculates physiological parameters and/or concentrations of tissue constituents using algorithms programmed into the spectroscopic analysis unit 24. The microprocessor 70 is connected to other component parts of the spectroscopic analysis unit 24, such as a ROM 72, a RAM 74, an actuator drive 76, a light drive unit 78, a decoder 80, an analog-to-digital converter 82, a display 84, an annunciation device 86, and a data port 87. The microprocessor 70 may also be connected to a wireless data communications transceiver 88 for use with a wireless network or communication infrastructure within a hospital, clinic, or emergency vehicle, or with a remote probe 122, as discussed with respect to FIG. 5. The ROM 72 holds the algorithms executed by the microprocessor 70. The RAM 74 stores entry parameters from the controls 68, digitized values from the analog-to-digital converter 82 for use in the algorithms, and results of the algorithms.

The microneedle system 50 has a probe 52 that may have actuators 56 for advancing the microneedle array 12 until the microneedles 18 pierce the epidermis 54 of a patient 48. The actuators 56 are controlled by the microprocessor 70 using the actuator drive 76. The probe may also have at least one emitter 90 configured to generate and transmit electromagnetic radiation, such as light, into optical fibers 92 which convey the light to the microneedles 18. The light is transmitted from the microneedles 18 into the epidermis 54 of a patient 48.

The light drive unit 78 in the spectroscopic analysis unit 24 controls the timing of the emitters 90. While the emitters are manufactured to operate at one or more certain wavelengths, variances in the wavelengths actually emitted may occur which may result in inaccurate readings. To help avoid inaccurate readings, an encoder 94 and the decoder 80 may be used to calibrate the spectroscopic analysis unit 24 to the actual wavelengths being used. The encoder 94 may be a resistor, for example, whose value corresponds to coefficients stored in the spectroscopic analysis unit 24. The coefficients may then be used in the algorithms. Alternatively, the encoder 94 may also be a memory device, such as an EPROM, that stores information, such as the coefficients themselves. Once the coefficients are determined by the spectroscopic analysis unit 24, they are inserted into the algorithms in order to calibrate the microneedle system 50.

The electromagnetic radiation from the emitters 90 is scattered and absorbed by the various constituents of the patient's tissues, such as water and protein. The microneedles 18 are connected to other optical fibers 96 which capture the reflected light and convey it back to at least one detector 98 configured to detect the scattered and reflected light and to generate a corresponding electrical signal. The detected signal from the detector 98 is carried from the probe 52 to a spectroscopic analysis unit 24 by a cable 60, for further processing. In the spectroscopic analysis unit 24, the signals are amplified and filtered by amplifier 100 and filter 101, respectively, before being converted to digital signals by the analog-to-digital converter 82. The signals may then be used in calculations performed by the microprocessor 70 and/or stored in RAM 74.

As multiple microneedles 18 may be individually operated and/or used in a spectroscopic analysis, numerous emitters 90 and detectors 98 may be provided. In order to interface with these, in one embodiment, the amp 100 and light drive 78 may contain multiplexing circuitry to control the particular emitter 90 and detector 98 associated with a single microneedle 18 in the microneedle array 12 or with a subset of the microneedles 18 of the microneedle array 12. Alternatively, in another embodiment, multiplexing circuitry may be contained in the circuitry of the emitters 90 and detectors 98, contained in the probe 52. This embodiment may minimize the number of separate electrical lines needed in the cable 60 connecting the probe 52 to the spectroscopic analysis unit 24.

The spectroscopic analysis unit 24 may be configured to display the calculated parameters on display 84. The display 84 may simply show the calculated oxygen saturation for a particular region of tissue where the microneedles 18 have taken measurements. As the oxygen saturation value under a particular microneedle 18 may not have any significance to a practitioner, the spectroscopic analysis unit 24 may be programmed to correlate the oxygen saturation measured at numerous microneedles 18 to generate a number indicative of, for example, the condition of the microvascularization. For example, a zero may be shown on the display 84 when the microvascularization matches a mean calculated for a healthy patient. Higher numbers may be displayed as the patient's condition more closely matches a mean calculated for the target condition, for example, sepsis. Alternatively, an annunciation device 86 may be used to audibly inform the practitioner of the severity of the condition or the initiation of drug delivery. Regardless of the manner of presentation, information generated by the spectroscopic analysis unit 24 is provided to a practitioner in a manner that may be quickly and easily understood.

In one implementation, the display 84 may show a map of the oxygen saturation across the microneedle array 12. Regions may be shaded or color coded to indicate relative values for the oxygen saturation. For example, normal oxygen saturation may be indicated by presenting the region with a green hue on the display 84. Alternatively, regions in which the oxygen saturation is low may be indicated by coloring the region a reddish hue, for example. As the oxygen saturation may change across an area being measured, the changes or differences in the oxygen saturation may be shown by a shading or coloring technique. Indeed, a single graphical image may demonstrate a wide range of shades or hues corresponding to a map of the oxygen saturation across the microneedle array 12 and/or to changes in oxygen saturation. Such an output display may be useful in determining the condition of the microvascularization, and may even be useful in visualizing the capillaries.

Further, the output from the algorithms may be used to control the administration of drugs. In an embodiment, the microprocessor 70 generates a control signal, and sends the signal to an I.V. pump 62 connected to the spectroscopic analysis unit 24 by a control line 42 connected to a data port 87. Upon receiving the signal, the I.V. pump may either start or stop pumping a drug from an I.V. bag 44 through tubing lines 46 to the probe 52 where it is administered to the patient through the microneedle array 12, as described below.

B. Operation of a Microneedle System

A sequence of operations that may be used to operate the microneedle system 50, in accordance with an embodiment of the present techniques, is shown in the block diagram of FIG.

4. This sequence is merely one example of a potential operational sequence, and is not intended to be limiting. Those skilled in the art will recognize that any number of other operational sequences may be programmed, as dictated by the needs of the patients being treated, and the configuration of the equipment selected.

In this exemplary sequence, as shown in block 104 the operator prepares the unit for use by filling the drug reservoirs, either external or self-contained within the probe, with the appropriate drugs and electrically, optically, and/or fluidically connecting the various components of the drug delivery system together. In block 106, the various components, such as the monitor, probe head, and/or drug delivery pump, are powered up, initializing the optics and other systems, and the appropriate treatment parameters are entered. Such treatment parameters may include drug type, dosage levels (or patient age, gender, weight, or other patient characteristics), and the physiological parameter or parameters to be tracked, among others. Physiological parameters that may be tracked in embodiments of the current invention include, but are not limited to, blood oxygen levels, blood sugar levels, tissue hydration, or any other appropriate physiological parameter. The probe 52 is then place in contact with the epidermis of the patient 54, and the treatment procedure is initiated, as shown in block 108.

After activation, in one embodiment as shown in block 110, the microneedle system 50 uses an automated sequence to advance the microneedle array 12 until the microneedles 18 pierce the stratum cornea of the epidermis 54. Once this contact has been detected, the spectroscopic analysis unit 24 analyzes the tissue composition around the microneedles, as shown in block 112. In block 114, the tissue composition values are evaluated based on the parameters previously entered by the user in block 106 to determine if administration of a drug is needed. As shown in block 116, if the administration of a drug is determined to be necessary, the unit may administer the drug. For example, in one embodiment, the drug may be administered by partially retracting the microneedles 18 from the epidermis and by applying the drug to the perfused epidermis through which the drug is infused. Alternatively, in other embodiments, if microneedles 18 having one or more passages are used, the unit may administer the compound through the passages 156 (see FIG. 7) of the microneedles 18. If administration of a drug is not needed, as shown in block 1118, the unit may stop an ongoing administration of a drug or may not initiate such an administration, and then return to block 112 to continue the tissue composition analysis. In either case, the spectroscopic analysis unit 24 may sound an alarm, if selected in block 106, to alert a practitioner of the change in conditions.

IV. A Wireless Microneedle System

Figure 5:
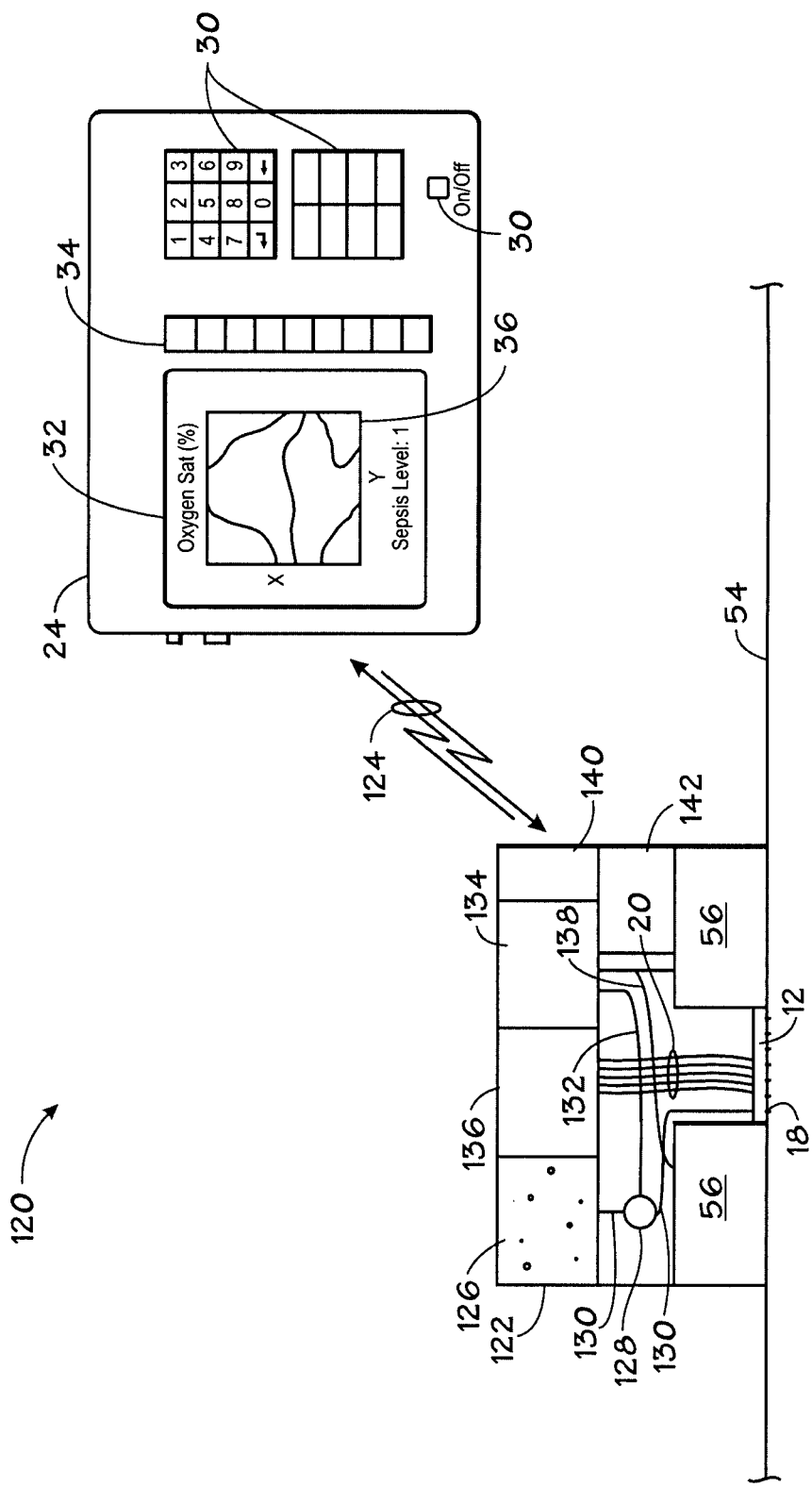
FIG. 5 is a perspective drawing of a system using a self contained probe, shown in a cut away view, for measuring a physiological parameter of a patient and delivering a drug in accordance with embodiments of the present technique.

In embodiments of the present techniques, a microneedle system may be implemented in a wireless configuration to minimize cabling around the patient. An example of such a system 120 is shown in FIG. 5. In this figure a self contained probe 122 may include the components and electronics necessary to control the spectroscopic analysis of tissue and the delivery of drugs underneath the microneedle array 12 without physical connection to other devices. Data analysis and control in this system 120 may be achieved through a wireless data link 124, which couples the spectroscopic analysis unit 24 with the remotely located probe 122 to allow control over the administration of a drug. The drug may be stored in an internal drug reservoir 126 contained within the probe 122. The drug may be pumped from the internal drug reservoir 126 to the microneedle array 12 using an internal drug delivery pump 128 that may also be contained within the probe 122.

Drug delivery lines 130 may connect the drug reservoir 126 to the pump 128 and the pump 128 to the microneedle array 12. The pump 128 may be powered by a control line 132 connecting the pump 128 to the probe control circuitry 134, which controls the delivery of the drug to the microneedle array 12. One or more microneedles 18 in the microneedle array 12 may be connected by optical fibers 20 to an optical system 136 which contains one or more emitters and one or more detectors. An electrical signal is generated by the optical system 136 in response to detected light. This electrical signal is sent to the spectroscopic analysis unit 24 over the wireless data link 124 for analysis. The control circuitry 134 may also be linked to the actuators 56 through power and control lines 138, enabling control of the motion of the microneedle array 12. The probe 122 may contain a power source 142, such as a battery, to power the control circuitry 134, optical system 136, and/or drug delivery pump 128.

In exemplary embodiments of the present techniques, when the remote probe 122 is placed on the epidermis 54 of a patient, a wireless data link 124 is established to the spectroscopic analysis unit 24. Under the control of the spectroscopic analysis unit 24 the remote probe 52 uses the actuators 56 to advance the microneedle array 12 until the microneedles 18 pierce the epidermis 54 of the patient 48. The probe 122, under the control of the spectroscopic analysis unit 24, may then be used to administer a drug through the epidermis 54 of the patient 48. For example, a drug may be infused through the epidermis by pooling the drug on the surface of the skin, followed by partial retraction of the microneedles 18, or by the use of microneedles 18 having one or more passages, such as microneedles having hollow cores. These techniques are discussed further in FIGS. 6 and 7 below.

VI. Drug Delivery Using Microneedles

Figure 6:
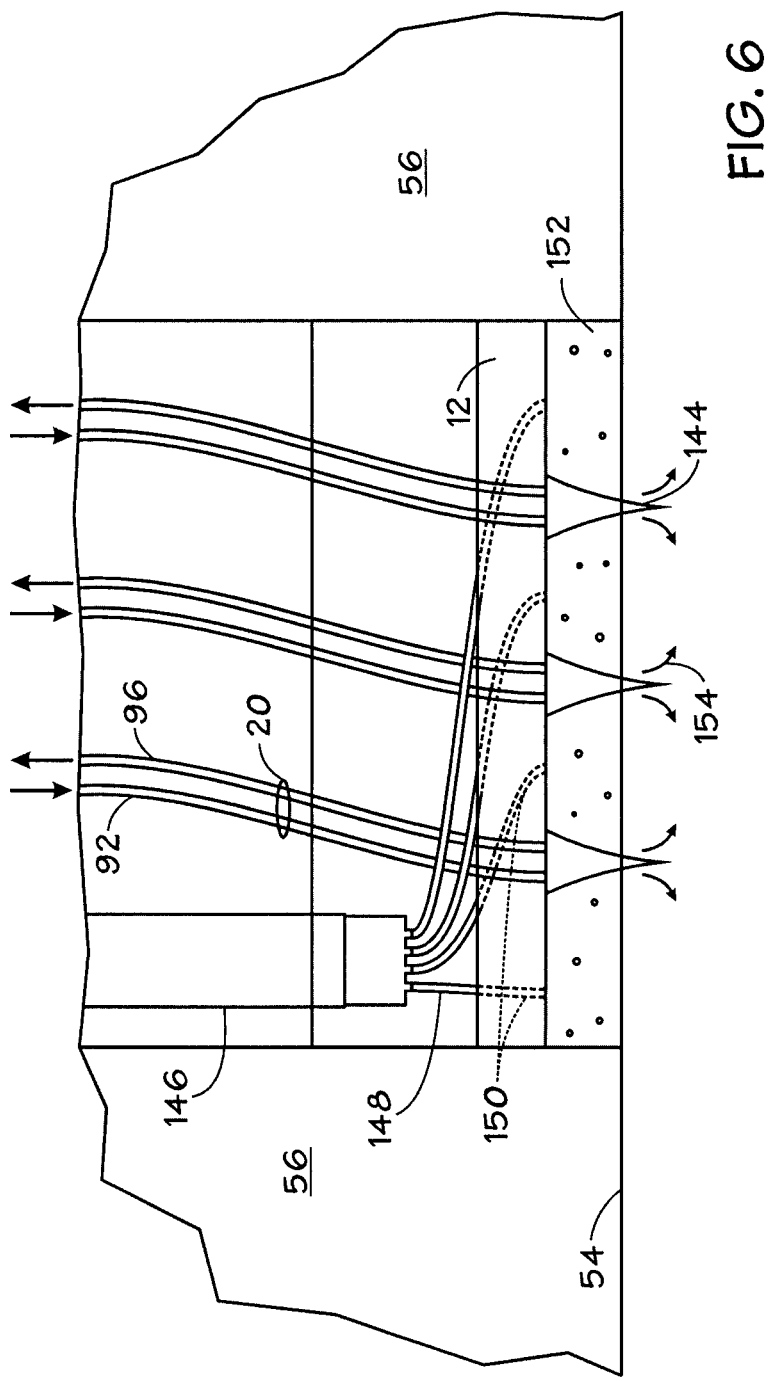
FIG. 6 is a close up, cut away view of a probe head that uses a microneedle array to increase the permeability of the skin for the delivery of a drug in accordance with an embodiment of the present techniques.

A technique for infusing drugs into a patient, in accordance with embodiments of the present invention, is shown by FIG. 6. This figure is a close up view of a microneedle array 12 after solid microneedles 144 have pierced the epidermis 54 of a patient. The solid microneedles 144 increase the permeability of the epidermis 54 allowing for the infusion of a drug. In this system a drug delivery line 146 may be divided into a series of drug delivery tubes 148 which go through the microneedle array 12 in drug delivery channels 150 to deliver a pool 152 of the drug onto the skin underneath the microneedle array 12. The solid microneedles 144 are partially retracted using the actuators 56 to leave breaks or passages in the epidermis 54 through which drug 154 may be infused through the epidermis 54. Optical fibers 20 may be connected to one or more of the microneedles 18 for spectroscopic analysis of the tissue. In this embodiment an optical fiber 92 may be used to channel light from emitters 90 into a solid microneedle 144 for delivering light to the epidermis 54 for the analysis and a separate optical fiber 96 may be used to take the light from the solid microneedle 144 to the detectors 98. In other embodiments, a single fiber optic wave guide may be used to channel light both to and from the solid microneedles 144.

Figure 7:
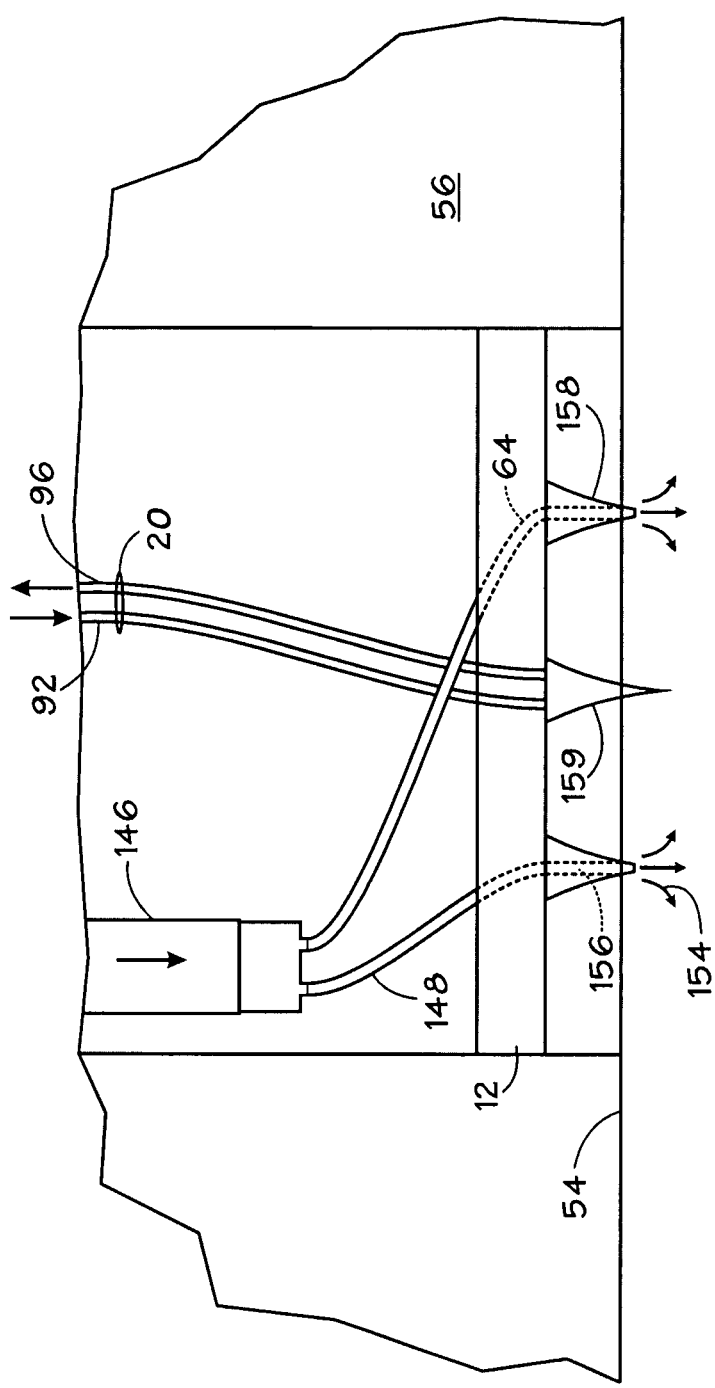
FIG. 7 is a close up, cut away view of a probe head that uses a microneedle array containing hollow microneedles to inject a drug in accordance with an embodiment of the present techniques.

Alternatively, as shown in FIG. 7, one or more passages 156 may be provided within hollow microneedles 158 through which the drug 154 may be introduced into the epidermis 54 of a patient. In this illustration a drug delivery line 146 divides into a series of drug delivery tubes 148, which connect to passageways or conduits 156 passing through the hollow microneedles 158. In this embodiment the microneedle array 12 is not retracted for administration of the drug 154 to the patient.

VII. Manufacturing Microneedles

Figure 8:
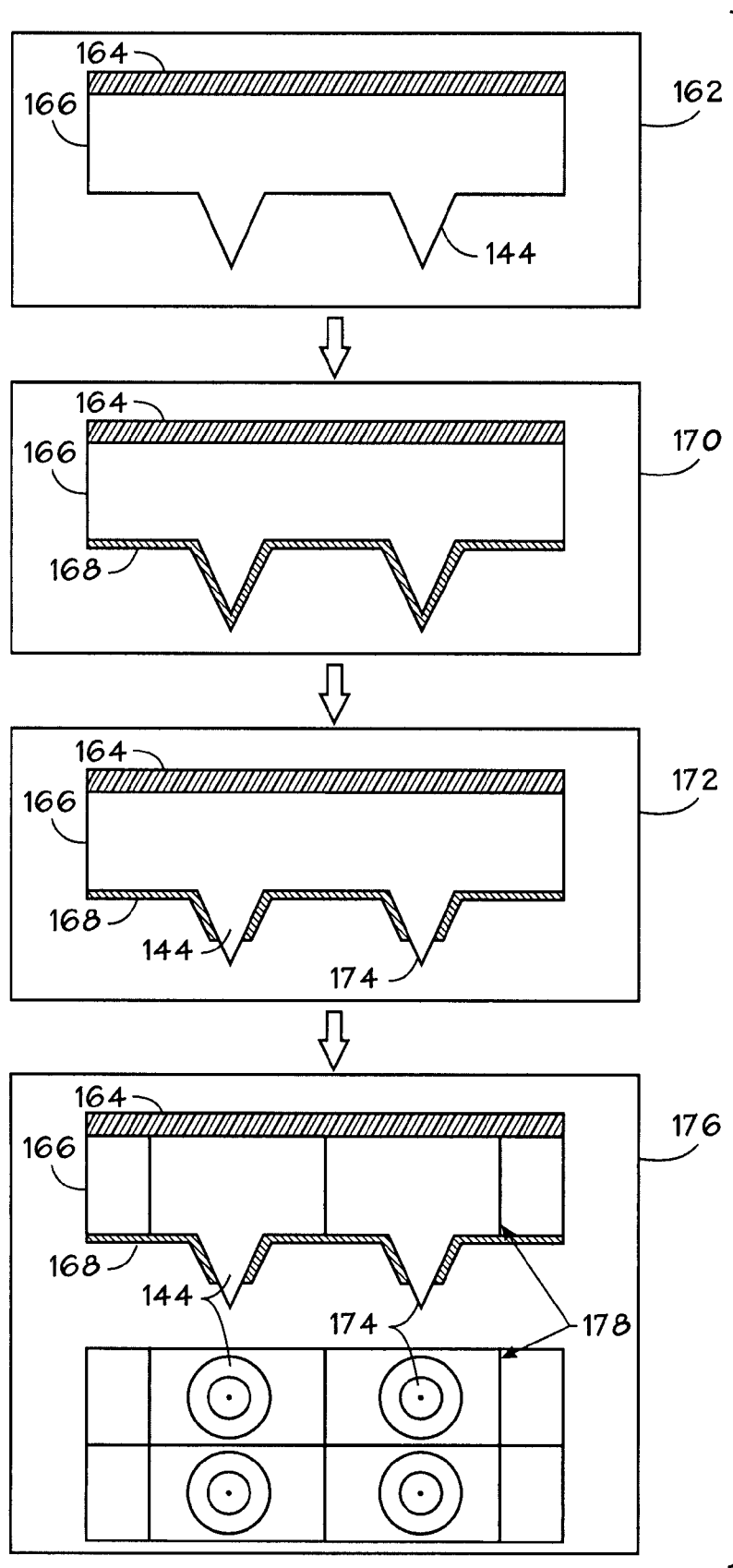
FIG. 8 is a block diagram of a procedure to make solid microneedles for coupling to optical fibers, in accordance with embodiments of the present technique.
Figure 9:
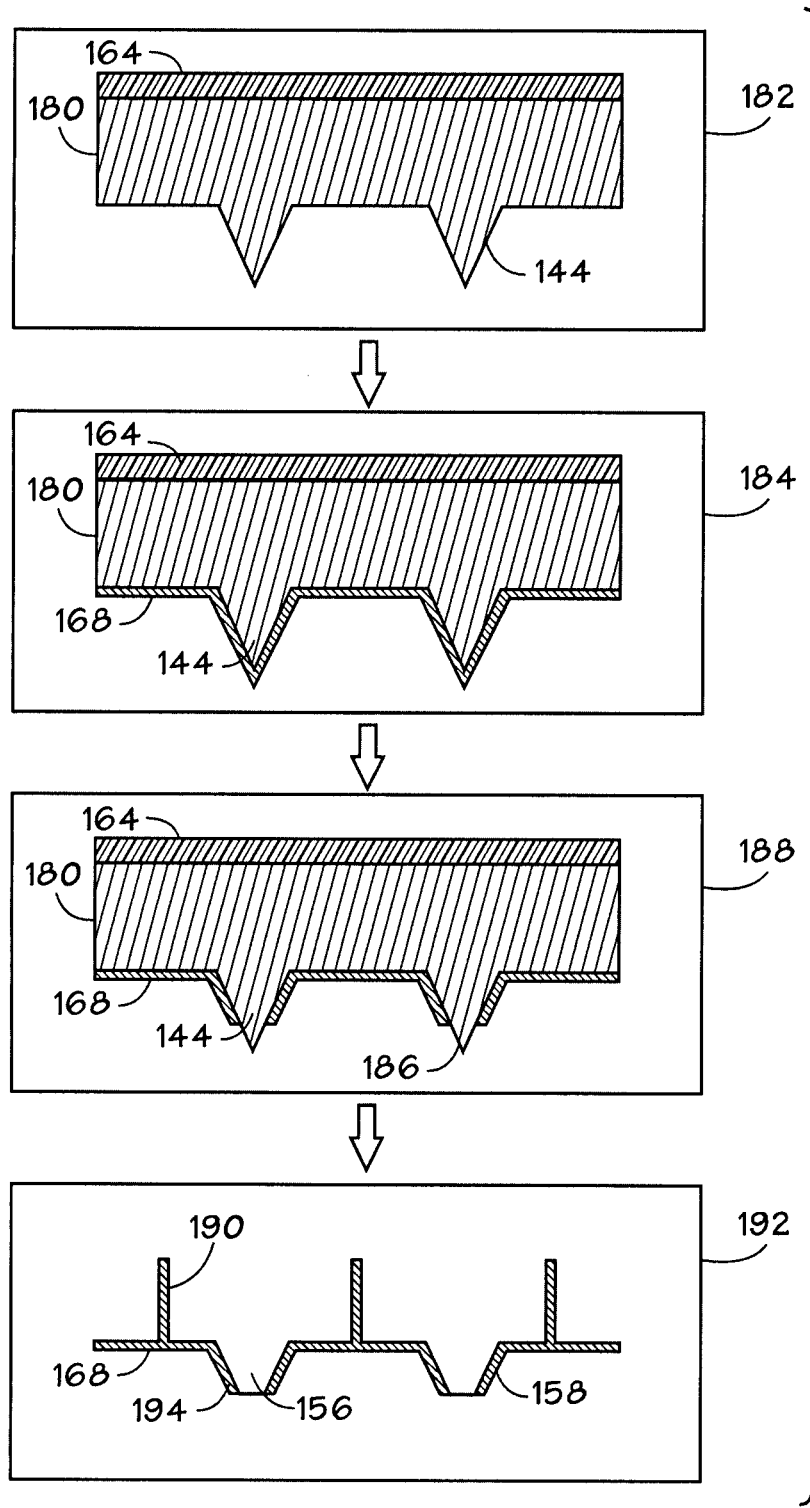
FIG. 9 is a block diagram of a procedure to make hollow microneedles, in accordance with embodiments of the present technique.

Exemplary procedures for making solid microneedles 144 or hollow microneedles 158 that may be used in embodiments of the present techniques are shown in FIGS. 8 and 9. FIG. 8 is a block diagram of an exemplary procedure for making solid microneedles 144. FIG. 9 is a block diagram of an exemplary procedure for making hollow microneedles 158 by removing material to form passageways or conduits 156 running axially along the hollow microneedles 158. Those skilled in the art will recognize that the following examples are only one technique for manufacturing microneedles, and that other techniques may be used. For example, microneedles may be formed using techniques borrowed from the manufacture of integrated circuits, such as chemical vapor deposition.

Turning to FIG. 8, in block 162, a substrate 164 is coated with an optically transmissive material 166. In embodiments of the present technique, the substrate may be, for example, a glass plate, a metal plate, a silicon wafer, or any other material that provides appropriate support during formation of the microneedle array 12. In embodiments of the present technique the optically transmissive material may be glass, silicone, poly(methyl methacrylate), polystyrene, poly(styrene acrylonitrile), polycarbonate, silicone, or any other appropriately transmissive material. Those skilled in the art will recognize that any number of other materials may be used in the embodiments of the current invention while remaining within the scope of the disclosure. From the optically transmissive material 166, solid microneedles 144 are formed either by molding using a template or by pulling partially molten material up from the surface.

After formation of the solid microneedles 144, the optically transmissive material 166 containing the solid microneedles 144 may have a metal layer 168 deposited over the top surface as shown in block 170. Metals that may be used to form the metal layer 168 include such metals as titanium, a titanium copper blend, or any other metal with appropriate physiological characteristics. As shown in block 172, the tips of each of the solid microneedles 144 may have the metal layer 168 removed by physical or chemical etching techniques to expose the transparent peak 174 at the end of each solid microneedle 144. In one embodiment, as shown in block 176, a metal grid 178 is imposed between the individual solid microneedles 144 to optically isolate each solid microneedle 144 from the adjacent microneedles 144. This may eliminate cross transmission of light and allow each solid microneedle 144 to function as an individual optical analysis unit. After the solid microneedles 144 have been formed, they may be coupled to optical fibers 20 for use in a microneedle array system 10 or they may be mounted in a probe 52 and 122 for use in a microneedle system 50. Alternatively, emitter 92 and detector 96 arrays may be mounted directly onto the substrate 164 and optically coupled to the solid microneedles 144 without the use of optical fibers 20.

A procedure for making hollow microneedles 158 having an axial passage or conduit 156, in accordance with embodiments of the present techniques, is shown in FIG. 9. Initially, solid microneedles 144 are formed from a material 180 that has been deposited on a substrate 164, as shown in block 182. This material 180 may be poly(methyl methacrylate), polystyrene, poly(styrene acrylonitrile), polycarbonate, silicone, polypropylene, polyethylene, or any other material that may be removed by etching or dissolution. After the formation of the solid microneedles 144, a metal layer 168 may be deposited over the top surface of the solid microneedles 144, as shown in block 184. The metal coating may then be etched away to reveal the tip 186 of the coating material 180, as shown in block 188.

A metal grid 190 is imposed separating each of the solid microneedles 144. In embodiments of the present invention, the metal grid 190 may be the same or similar to that discussed with respect to block 176 of FIG. 8. In other embodiments, the metal grid 190 may be thicker to support the array after the material 180 and substrate 164 are removed. As shown in block 192, the substrate 164 and/or the coating material 180 may be dissolved or etched away leaving a structure of hollow microneedles 158 having hollow passageways 156 or spaces defined by the microneedle surface 194. After the hollow microneedles 158 are formed, they may be mounted in a probe 52, 122 and connected to drug delivery lines 148 for use in the microneedle system 50.

While the invention may be susceptible to various modifications and alternative forms, specific embodiments have been shown by way of example in the drawings and will be described in detail herein. However, it should be understood that the invention is not intended to be limited to the particular forms disclosed. Furthermore, those skilled in the art will recognize that the techniques discussed may be used in other number of medical settings, including for monitoring internal tissue composition during surgical procedures. Indeed, the invention is to cover all modifications, equivalents and alternatives falling within the spirit and scope of the invention as defined by the following appended claims.

What is claimed is:

1. An array of microneedles, comprising:
   one or more optically transmissive microneedles, wherein at least one of the optically transmissive microneedles is capable of transmitting light into a tissue and at least one of the optically transmissive microneedles is capable of receiving the light returning from the tissue and wherein at least one of the optically transmissive microneedles is coupled by one or more optical fibers to at least one of an optical emission device or an optical detection device.

2. The array of microneedles of claim 1 comprising one or more hollow microneedles.

3. The array of microneedles of claim 2 wherein the one or more hollow microneedles are capable of injecting a drug into a patient.

4. The array of microneedles of claim 1 wherein at least one of the microneedles comprises a continuous solid structure.

5. The array of microneedles of claim 4 wherein the microneedles comprising the respective solid structures are made from an optically transmissive material.

6. The array of microneedles of claim 1 wherein at least one of the microneedles is configured to enhance the permeability of the epidermis of a patient.

7. The array of microneedles of claim 1 wherein the array is configured to be moved by an actuator unit.

8. The array of microneedles of claim 7 wherein the actuator unit is configured to enable motion control of the array accurate to about 10 micrometers or less.

9. The array of microneedles of claim 1 wherein one or more of the microneedles are coated with a drug.

* * * * *